United States Patent [19]

Peindl et al.

[11] Patent Number: 5,538,887
[45] Date of Patent: Jul. 23, 1996

[54] CELL CULTURE APPARATUS HAVING SMOOTH SURFACE FOR CELL GROWTH THEREON

[75] Inventors: Richard D. Peindl; Warren K. Ramp, both of Charlotte, N.C.

[73] Assignee: Charlotte-Mecklenburg Hospital Authority, Charlotte, N.C.

[21] Appl. No.: 198,982

[22] Filed: Feb. 18, 1994

[51] Int. Cl.$^6$ .................................................... C12M 3/00
[52] U.S. Cl. ............................... 435/240.243; 435/240.1; 435/240.23; 435/284.1; 435/309.1
[58] Field of Search ....................... 359/398, 396; 435/284, 285, 297, 299, 301, 240.23, 240.243, 240.1; 623/1, 66; 427/2.24, 2.25, 491

[56] References Cited

U.S. PATENT DOCUMENTS

| | | | |
|---|---|---|---|
| 3,939,834 | 2/1976 | McMahon | 604/403 |
| 3,976,547 | 8/1976 | McAleer et al. | 435/285 |
| 4,448,884 | 5/1984 | Henderson | 435/240.24 |
| 4,661,407 | 4/1987 | Henderson | 428/403 |
| 4,919,659 | 4/1990 | Horbett | 623/1 |
| 5,018,847 | 5/1991 | Ojima et al. | 359/398 |
| 5,134,070 | 7/1992 | Casnig | 435/173.6 |

FOREIGN PATENT DOCUMENTS

| | | |
|---|---|---|
| 3938632C1 | 3/1991 | Germany . |
| 63196285A | 8/1988 | Japan . |

OTHER PUBLICATIONS

Gabriel, et al., Site-Specific Adhesion of *S. epidermidis* in Ti–Al–V Metal Systems.
Puleo, et al., Examination of osteoblast–orthopaedic biomaterial interactions using molecular techniques, *Biomaterials*, 1993, vol. 14, No. 2, pp. 111–114.
Vrouwenvelder, et al., Histological and biochemical evaluation of osteoblasts cultured on bioactive glass, hydroxylapatite, titanium alloy, and stainless steel, *Journal of Biomedical Materials Research*, vol. 27, pp. 465–475, 1993.

Murray, et al., The Influence of the Surface Energy and Roughness of Implants on Bone Resorption, *The Journal of Bone and Joint Surgery*, vol. 71–B, No. 4, Aug., 1989, pp. 632–637.
Cooke Vacuum Products, Inc., Model–CV–301 3" Portable High Vacuum Evaporator/Pump Station, Section 6–1 Mar. 1992 2M.
*Culture Surfaces Coated with Various Implant Materials Affect Chondrocyte Growth and Metabolism*, J. Hambleton et al., Journal of Orthopaedic Research, vol. 12, No. 4, 1994, pp. 542–552.
*Keynote Address: Biological Implications*, B. D. Boyan et al.; Biological Material, and Mechanical Considerations of Joint Replacement, 1993, pp. 27–34.
*Modulation of Chondrocyte Differentiation by Growth on Sputter–Coated Surfaces*, J. Hambleton et al., J. Dent. Res. 72 (LADR Abstracts) 1993, 2292.

Primary Examiner—Esther M. Kepplinger
Assistant Examiner—Milton I. Cano
Attorney, Agent, or Firm—Bell, Seltzer, Park & Gibson

[57] ABSTRACT

A cell culture apparatus includes a substrate, and an inorganic film on the substrate and having a relatively smooth surface for cell growth thereon. Moreover, the relatively smooth surface has a relatively low predetermined surface roughness so that cells grown thereon adhere by chemical adhesion rather than by mechanical interlocking. In other words, the predetermined surface roughness defines surface indentations smaller than a size of corresponding cells to be grown thereon. Accordingly, the interaction between various inorganic materials and cells may be studied based upon chemical adhesion rather than mechanical interlocking. The predetermined surface roughness is preferably less about 10 μm root-mean-square, and more preferably less than about 1 μm root-mean-square. The relatively smooth growth surface is preferably obtained by thermal vacuum evaporation and deposition, followed by annealing of the as-deposited film.

17 Claims, 1 Drawing Sheet

CELL CULTURE APPARATUS HAVING SMOOTH SURFACE FOR CELL GROWTH THEREON

FIELD OF INVENTION

The present invention relates to the field of biology and microbiology and, more particularly, to an apparatus and method for facilitating culturing of cells.

BACKGROUND OF THE INVENTION

Research laboratories throughout the world are currently conducting tests to study cell growth under different conditions. For example, tests are being conducted relating to control of surface topography of a cell growth surface to optimize the output of cells within a finite area. An exemplary purpose of such testing is to decrease the costs of cells used in vaccine production. For example, U.S. Pat. No. 3,976,547 to McAleer et al. discloses that a cell growth surface having irregularities increases the surface area available for cell growth. McAleer et al. obtain the irregular surface area by sintering or sputter coating metal, glass, ceramic or plastic onto a suitable substrate.

Alternatively, research is being conducted to determine how various cells interact with a wide variety of inorganic materials such as ceramics, glass, plastics and metals. The purpose of such study is as varied as the cells and inorganic materials being tested. For example, research is currently being conducted in the medical field in an attempt to locate a material that would be well suited for use in implants.

Implants are commonly inserted or grafted into the human body for either prosthetic, therapeutic, diagnostic, cosmetic or experimental purposes. Many of these implants have traditionally been made of inorganic materials that were originally developed and used for non-medical or unrelated purposes, such as aerospace applications. As a result, the inorganic materials presently available for medical implants do not necessarily have the optimal mechanical properties and inert behavior characteristics desirable for use within the body. For instance, a skeletal prostheses should be able to withstand extreme bending, buckling and torsional forces, while maintaining the ability to dampen mechanical vibrations, as well as meet stringent requirements with respect to surface hardness and abrasion resistance. In addition to the mechanical stability required, the implant should also be chemically resistant to corrosion resulting from bodily fluids and tissues, be non-toxic and meet the electro-conductivity requirements.

Because an implant is made of inorganic materials foreign to the body, it is important that the implant be biocompatible, that is, capable of co-existing with the living tissue in the surrounding human environment. At present, inorganic materials which have currently been tested and used may not be optimally suited for implants based upon their mechanical properties and inert behavior within the body. Unfortunately, relatively high costs are associated with the research and development of inorganic materials for implants.

Assessment of the interaction between cells and a wide variety of inorganic materials is an important diagnostic tool in determining the acceptability of a particular inorganic material for use in implants. Several tests including biocompatibility, cell integration, cell inductiveness, cell conductiveness, corrosiveness and toxicity may be performed to evaluate the interaction of cells with a potential implant material. To conduct the above reference tests and/or related tests the inorganic material to be tested is typically placed within a receptacle and thereby subjected to a controlled environment for interaction with cells.

At present, the desired inorganic material, for example ceramics or metals, are manufactured by conventional techniques such as casting, forging or sintering, and are then sectioned into a desired number of wafers. The wafers are mechanically ground and polished, then degreased, cleaned, passivated, sterilized and dried. Examples of this form of wafer preparation may be seen in an article by D. A. Puleo, et al. entitled *Examination of Osteoblast-Orthopaedic Biomaterial Interactions Using Molecular Techniques* appearing in Biomaterials, Vol. 14, No. 2, pp. 111–114 (1993) and in an article written by W. C. A. Vrouwenvelder, et al. entitled *Histological and Biochemical Evaluation of Osteoblast Cultured on Bioactive Glass, Hydroxyapatite, Titanium Alloy and Stainless Steel* appearing in Journal of Biomedical Materials Research, Vol. 27, pp. 465–475 (1993). The problem with using wafers for testing the interaction of cells with each of the respective inorganic materials is the cost associated with producing or purchasing such wafers, the delicacy in which they must be handled, as well as the associated time and effort involved preparing the wafers for use.

The interaction of cells with the various implant materials is determined based upon a number of factors. One such factor is the degree of roughness of the surface of the material. If the surface topography is rough, the cells rely on mechanical interlocking or interdigitation to attach to the growth surface. Mechanical interlocking is schematically illustrated by the greatly enlarged portion of a prior art cell culture apparatus 5 shown in FIG. 1. The cell culture apparatus 5 includes a metal layer 6 on a substrate 7, and wherein the cell growth surface 8 of the metal layer has pockets or indentations of a size equal to or larger than the size of a cell 9. Accordingly, the entire cell 9 or an extension thereof fits within and attaches to the pocket defined on the growth surface via mechanical interlocking.

To date, testing done relating to cell growth has focused primarily on mechanical interlocking of the cell with the growth surface. Or more to the point, current research has tested factors effecting cell growth in reliance on mechanical interlocking. Along these lines, U.S. Pat. No. 5,018,847 to Ojima et al., for example, discloses an instrument for cultivation and observation of cells using a transparent biocompatible ceramic coating. The growth surface is preferably formed by flame spray coating or plasma spray coating which are typically used to produce a relatively rough surface, although Ojima et al. fails to suggest surface roughness as being of interest. Along these lines, U.S. Pat. No. 3,939,834 to McMahon discloses a container which is coated on the interior surface with a coherent barrier layer of metal formed by sputtering to thereby form an impermeable barrier between the receptacle interior walls and the receptacle contents.

SUMMARY OF THE INVENTION

In view of the foregoing background, it is therefore an object of the present invention to provide a cell culture apparatus and associated method that has a cell growth surface which relies on chemical adhesion between the cells and the growth surface rather than mechanical interlocking.

This and other objects, features and advantages according to the invention are provided by a cell culture apparatus including a substrate, and an inorganic film on the substrate and having a relatively smooth surface for cell growth thereon. Moreover, the relatively smooth surface has a relatively low predetermined surface roughness so that cells grown thereon adhere by chemical adhesion rather than by mechanical interlocking. In other words, the predetermined surface roughness defines surface indentations smaller than a size of corresponding cells to be grown thereon. Accordingly, the interaction between various inorganic materials and cells may be studied based upon chemical adhesion rather than mechanical interlocking.

The predetermined surface roughness is preferably less about 10 µm root-mean-square, and more preferably less than about 1 µm root-mean-square. Even smoother surfaces may be produced in accordance with method aspects of the present invention.

Another aspect of the invention facilitates evaluation of cells within the cell culture apparatus by providing a transparent substrate and a sufficiently thin inorganic film so that the film is also transparent. The inorganic film may preferably be a metal, such as commercially pure titanium, or may be a ceramic, such as hydroxyapatite (HA). The inorganic film is desirably relatively thin and preferably has a thickness less than about 0.5 µm. To enhance the durability of such a thin metal film, it is preferred to anneal the as-deposited metal film to relieve stresses in the film.

As would be readily understood by those skilled in the art, the substrate is preferably a portion of a receptacle, such as a microscope slide or bottom of a petri dish as may be commonly used for cell culturing. Accordingly, the substrate is preferably a plastic material.

A method aspect of the present invention is for making the cell culture apparatus and includes the steps of: providing a substrate, and depositing an inorganic film on the substrate to have a relatively smooth surface with a predetermined surface roughness so that cells grown thereon adhere by chemical adhesion rather than by mechanical interlocking. The step of depositing the inorganic film preferably includes depositing same by thermal vacuum evaporation of the inorganic material. Annealing the as-deposited inorganic film reduces stresses and provides a more durable film. Accordingly, a predetermined surface roughness of less than about 10 µm root-mean-square, and more preferably less than about 1 µm root-mean-square may be readily achieved. This relatively smooth surface defines surface indentations smaller than a size of corresponding cells to be grown thereon.

This deposition technique not only allows the inorganic material to be deposited directly onto the substrate, but also avoids having to prepare a discrete wafer of the desired inorganic material prior to its deposition. This further eliminates the time-consuming and expensive steps of polishing, cleaning, sterilizing and drying as needed for conventional wafers. It also avoids having to remove the processing residues and debris that would otherwise contaminate the cell growth surface. Further, researchers may readily prepare experiments with a desired inorganic material and can create an inorganic film at a relatively low cost and in a relatively short period of time. In addition, the number of receptacles which can simultaneously be prepared is greatly increased and a sterilized cell culture apparatus is readily produced in accordance with the present invention.

The method preferably includes providing a transparent substrate, and the step of depositing the inorganic material film preferably includes depositing the film to predetermined thickness so as to be transparent to facilitate evaluation of cells by observation therethrough. For example, the thickness may be less than about 0.5 µm, while substantially thinner films may be readily produced by thermal vacuum evaporation and deposition.

BRIEF DESCRIPTION OF THE DRAWINGS

Some of the objects, features and advantages of the present invention having been stated, others will appear as the description proceeds, when taken in conjunction with the accompanying drawings in which.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in different forms and should not be construed as limited to the embodiments set forth herein. Rather, the illustrative embodiments are provided so that this disclosure will be thorough and complete, and will fully convey the scope of the invention to those skilled in the art. Like numbers refer to like elements throughout.

Figure 2:
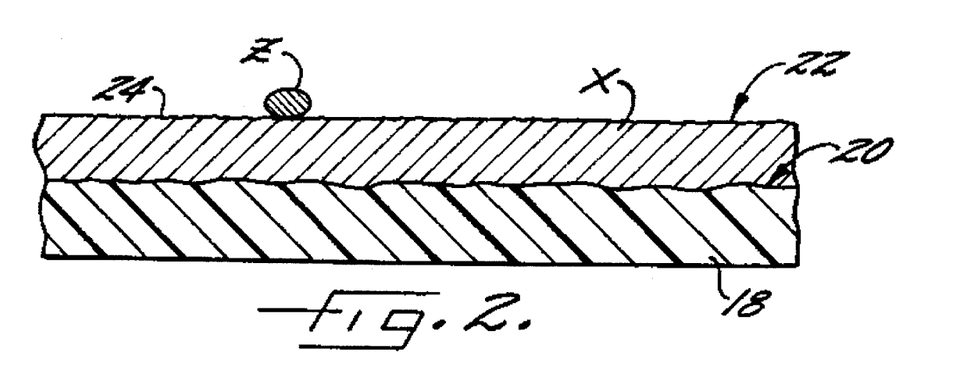
FIG. 2 is a perspective view of a cell culture apparatus in accordance with the present invention and having a relatively smooth cell growth surface.
Figure 3:
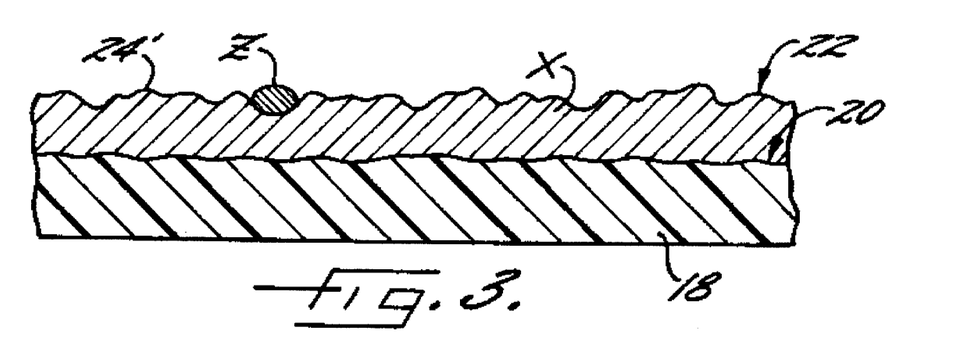
FIG. 3 is a greatly enlarged schematic cross-sectional view of the cell culturing apparatus according to the invention taken along lines 3—3 of FIG. 2.

Referring now to FIGS. 2 and 3, the cell culture apparatus 10 according to the invention is explained. The illustrated apparatus 10 includes a receptacle or container which may be manufactured from any of the known and accepted materials for biological testing purposes, such as plastic, as would be readily understood by those skilled in the art. In the illustrated embodiment, the receptacle is a plastic petri dish having a bottom 17, a circular sidewall 15 extending upwardly from the bottom, and a top or cover 14. It is to be understood however, that it is also possible to use a number of different receptacles, such as test tubes, multi-well culture plates, flasks, microscope slides, and/or beakers and still remain within the spirit of the invention.

The bottom 17 defines a substrate on which a film 16 of inorganic material, such as metal or ceramic, is deposited. For example, the metal may be commercially pure titanium, while the ceramic may be hydroxyapatite, for example, as would be readily appreciated by those skilled in the art. The inorganic material is preferably deposited by thermal vacuum evaporation and deposition, as would also be readily understood by those skilled in the art. This technique allows the film 16 to be deposited directly onto the surface of the substrate, without first requiring preparation of an inorganic material in a wafer form as by conventional manufacturing techniques. It is to be understood that other deposition techniques may be used to deposit the film 16 of inorganic material onto the substrate, so long as the material is relatively smooth to permit chemical adhesion of the cells to the desired smoothness and/or the desired thickness, as described in detail below.

Figure 1:
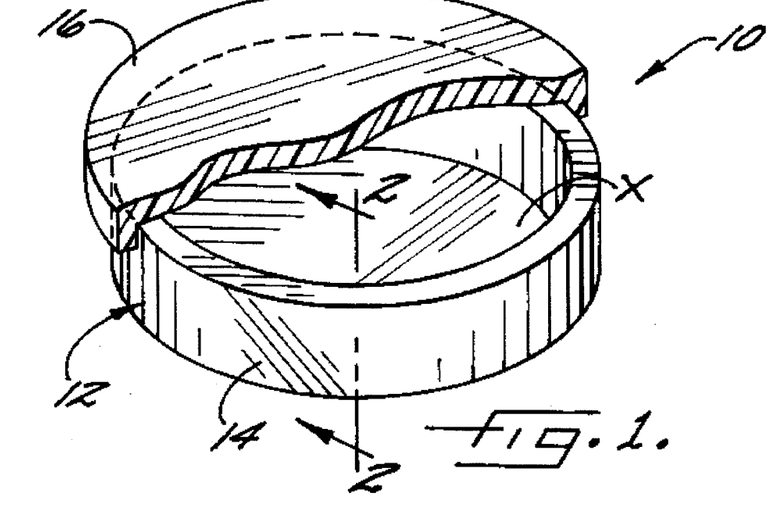
FIG. 1 is a greatly enlarged schematic cross-sectional view of a portion of a cell culture apparatus as in the prior art and having a relatively rough cell growth surface.

The film 16 of inorganic material has a relatively smooth surface 18 for cell growth so that cells 19 grown thereon adhere primarily by chemical adhesion rather than by mechanical interlocking (FIG. 1). Accordingly, the relatively smooth surface topology facilitates chemical adhesion as the primary means for bonding between the film 16 and the cells 19, and thereby permits the study of cell growth and interaction without the influence of mechanical interlocking between the film and the cells.

The surface 18 is sufficiently smooth when the size of the corresponding cells 19 to be grown is less than the size of pockets, grooves, cavities or other similar indentations occurring in the surface. When this condition is achieved, mechanical interlocking is no longer possible and the cells 19 primarily rely on chemical adhesion to attach or adhere to the smooth surface 18. It is understood that the sizes of the cells 19 and indentations in the surface 18 may vary depending on the various types of cells and the inorganic material being tested. At present, it is believed that a smooth surface, depending on the corresponding size of the cells to be used, is a surface topography having a predetermined roughness of less than about 10 μm root-mean-square, and more preferably less than about 1 μm root-mean-square. Applicants believe that if the smoothness of the inorganic material being tested can be selectively controlled within such a finite upper limit, it will be possible to obtain more accurate results in other tests important to the determination of an inorganic material optimally suited for use in implants, for example. According to a method aspect of the present invention, a surface roughness on the order of 0.01 μm root-mean-square and lower may be readily achieved.

Based upon current understanding of cell growth, when the surface topography of the growth surface 18 is relatively smooth as described above, it is theorized by applicants without there wishing to be bound thereto that cells can only attach to the growth surface by means of chemical adhesion. Applicants are unaware of any research which has been conducted to specifically test the factors affecting chemical adhesion of cells to inorganic materials. Applicants are however aware of an article written by D. W. Murray et al., entitled *The Influence of the Surface Energy and Roughness of Implants on Bone Resorption* appearing in the Journal of Bone and Joint Surgery, Vol. 71-B, pp. 632–637 (1989) which discloses that surface roughness had an effect on cell growth for implants; however, the authors were unable to qualify or quantify which factors were important or effected by the surface topography of the growth surface, let alone how to control these factors.

In the illustrated embodiment as shown in FIGS. 2 and 3, the film 16 of inorganic material is preferably deposited so that it has a thickness of less than about 0.5 μm. This thickness is thick enough to achieve the desired surface smoothness, yet thin enough to allow the cells to interact with the inorganic material. In addition, the thickness may be readily controlled, based upon the particular inorganic material, so that the film 16 is transparent to facilitate observation through a transparent substrate and the film 16. Although transparency is not an essential element of the present invention, it is an appreciable advantage to the extent that it allows the interaction of the cells to be evaluated on an inverted microscope without disrupting continued culturing of the cells. Unfortunately, existing conventional wafer forming techniques make it difficult and costly to obtain a wafer having a surface topography with the desired smoothness and obtain a wafer which is sufficiently thin so as to be transparent.

The method according to the present invention is for making the cell culture apparatus 10 as described above and includes the steps of: providing a substrate, and depositing an inorganic film 16 on the substrate to have a relatively smooth surface 18 with a predetermined surface roughness so that cells 19 grown thereon adhere by chemical adhesion rather than by mechanical interlocking. The step of depositing the inorganic film 16 preferably includes depositing same by thermal vacuum evaporation of the inorganic material as would be readily understood by those skilled in the art. Annealing the as-deposited inorganic film reduces stresses and provides a more durable film. Accordingly, a predetermined surface roughness of less than about 10 μm root-mean-square, and more preferably less than about 1 μm root-mean-square may be readily achieved. This relatively smooth surface 18 defines surface indentations smaller than a size of corresponding cells 19 to be grown thereon. This deposition technique not only allows the inorganic material to be deposited directly onto the substrate, but also avoids having to prepare a conventional discrete wafer of the desired material by polishing, cleaning, sterilizing and drying. A number of cell culture apparatuses may be simultaneously prepared using thermal vacuum evaporation to thereby reduce manufacturing cost, while providing sterilized cell culture apparatuses.

The method preferably includes providing a transparent substrate, and the step of depositing the inorganic material film 16 preferably includes depositing the film to predetermined thickness so as to be transparent to facilitate evaluation of cells by observation therethrough. For example, the thickness may be less than about 0.5 μm, while substantially thinner films 16 may be readily produced by thermal vacuum evaporation and deposition.

It is possible to use conventional masking techniques in combination with the thermal vacuum deposition to obtain a cell culture apparatus with more than one inorganic film over the substrate, such as if a comparison of the interaction of the cells with more than one metal is desired. In such an event, the inorganic material may be deposited onto the substrate either in strips, quadrants or whatever pattern is desired, and as would be readily understood by those skilled in the art.

Many modifications and other embodiments of the invention will come to mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

What is claimed is:

1. A cell culture apparatus comprising:

a substrate; and an inorganic film on said substrate and said inorganic film having a smooth surface for promoting cell growth thereon by chemical adhesion, the smooth surface having a surface roughness less than about 10 μm root-mean-square defining surface indentations smaller than a size of corresponding cells to be grown thereon so that cells grown thereon adhere by chemical adhesion rather than by mechanical interlock.

2. A cell culture apparatus according to claim 1 wherein said surface roughness is less than about 1 μm root-mean-square.

3. A cell culture apparatus according to claim 1 wherein said substrate is transparent, and wherein said inorganic film is thin so as to be transparent to facilitate evaluation of cells by observation therethrough.

4. A cell culture apparatus according to claim 1 wherein said inorganic film has a thickness of less than about 0.5 μm.

5. A cell culture apparatus according to claim 1 wherein said inorganic film comprises metal.

6. A cell culture apparatus according to claim 5 wherein said metal film is annealed.

7. A cell culture apparatus according to claim 1 wherein said inorganic film comprises ceramic.

8. A cell culture apparatus according to claim 1 wherein said substrate comprises plastic.

9. A cell culture apparatus according to claim 1 further comprising sidewalls extending upwardly from said substrate to thereby define a petri dish.

10. A cell culture apparatus comprising:

a substrate; and an inorganic film having a thickness of less than about 0.5 µm on the substrate to have a smooth surface with a predetermined surface roughness defining surface indentations smaller than the size of corresponding cells to be grown thereon so that cells grown thereon adhere by chemical adhesion rather than by mechanical interlock.

11. A cell culture apparatus according to claim 10 wherein said surface roughness is less than about 10 µm root-mean-square.

12. A cell culture apparatus according to claim 10 wherein said substrate is transparent, and wherein said inorganic film is thin so as to be transparent to facilitate evaluation of cells by observation therethrough.

13. A cell culture apparatus according to claim 10 wherein said inorganic film comprises metal.

14. A cell culture apparatus according to claim 13 wherein said metal film is annealed.

15. A cell culture apparatus according to claim 10 wherein said inorganic film comprises ceramic.

16. A cell culture apparatus according to claim 10 wherein said substrate comprises plastic.

17. A cell culture apparatus according to claim 10 further comprising sidewalls extending upwardly from said substrate to thereby define a petri dish.

* * * * *

UNITED STATES PATENT AND TRADEMARK OFFICE
CERTIFICATE OF CORRECTION

PATENT NO.   : 5,538,887
DATED        : July 23, 1996
INVENTOR(S)  : Peindl, et. al.

It is certified that error appears in the above-identified patent and that said Letters Patent is hereby corrected as shown below:

Drawings:

The Title page should be deleted and substitute therefor the attached Title page.

Delete Drawing sheets 1-3, and substitute therefor the Drawing sheets, consisting of Figs. 1-3, as shown on the attached pages.

Signed and Sealed this

First Day of April, 1997

BRUCE LEHMAN

*Attest:*

*Attesting Officer*   *Commissioner of Patents and Trademarks*

United States Patent
Peindl et al.

Patent Number: 5,538,887
Date of Patent: Jul. 23, 1996

[54] CELL CULTURE APPARATUS HAVING SMOOTH SURFACE FOR CELL GROWTH THEREON

[75] Inventors: Richard D. Peindl; Warren K. Ramp, both of Charlotte, N.C.

[73] Assignee: Charlotte-Mecklenburg Hospital Authority, Charlotte, N.C.

[21] Appl. No.: 198,982

[22] Filed: Feb. 18, 1994

[51] Int. Cl.$^6$ ............................................ C12M 3/00
[52] U.S. Cl. .......................... 435/240.243; 435/240.1; 435/240.23; 435/284.1; 435/309.1
[58] Field of Search .............................. 359/398, 396; 435/284, 285, 297, 299, 301, 240.23, 240.243, 240.1; 623/1, 66; 427/2.24, 2.25, 491

[56] References Cited

U.S. PATENT DOCUMENTS

| | | | |
|---|---|---|---|
| 3,939,834 | 2/1976 | McMahon | 604/403 |
| 3,976,547 | 8/1976 | McAleer et al. | 435/285 |
| 4,448,884 | 5/1984 | Henderson | 435/240.24 |
| 4,661,407 | 4/1987 | Henderson | 428/403 |
| 4,919,659 | 4/1990 | Horbett | 623/1 |
| 5,018,847 | 5/1991 | Ojima et al. | 359/398 |
| 5,134,070 | 7/1992 | Casnig | 435/173.6 |

FOREIGN PATENT DOCUMENTS

| | | |
|---|---|---|
| 3938632C1 | 3/1991 | Germany. |
| 63196285A | 8/1988 | Japan. |

OTHER PUBLICATIONS

Gabriel, et al., Site-Specific Adhesion of *S. epidermidis* in Ti-Al-V Metal Systems.

Pulco, et al., Examination of osteoblast-orthopaedic biomaterial interactions using molecular techniques, *Biomaterials*, 1993, vol. 14, No. 2, pp. 111–114.

Vrouwenvelder, et al., Histological and biochemical evaluation of osteoblasts cultured on bioactive glass, hydroxylapatite, titanium alloy, and stainless steel. *Journal of Biomedical Materials Research*, vol. 27, pp. 465–475, 1993.

Murray, et al., The Influence of the Surface Energy and Roughness of Implants on Bone Resorption, *The Journal of Bone and Joint Surgery*, vol. 71-B, No. 4, Aug., 1989, pp. 632–637.

Cooke Vacuum Products, Inc., Model-CV-301 3" Portable High Vacuum Evaporator/Pump Station, Section 6-1 Mar. 1992 2M.

*Culture Surfaces Coated with Various Implant Materials Affect Chondrocyte Growth and Metabolism*, J. Hambleton et al., Journal of Orthopaedic Research, vol. 12, No. 4, 1994, pp. 542–552.

*Keynote Address: Biological Implications*, B. D. Boyan et al.; Biological Material, and Mechanical Considerations of Joint Replacement, 1993, pp. 27–34.

*Modulation of Chondrocyte Differentiation by Growth on Sputter-Coated Surfaces*, J. Hambleton et al., J. Dent. Res. 72 (LADR Abstracts) 1993, 2292.

*Primary Examiner*—Esther M. Kepplinger
*Assistant Examiner*—Milton I. Cano
*Attorney, Agent, or Firm*—Bell, Seltzer, Park & Gibson

[57] ABSTRACT

A cell culture apparatus includes a substrate, and an inorganic film on the substrate and having a relatively smooth surface for cell growth thereon. Moreover, the relatively smooth surface has a relatively low predetermined surface roughness so that cells grown thereon adhere by chemical adhesion rather than by mechanical interlocking. In other words, the predetermined surface roughness defines surface indentations smaller than a size of corresponding cells to be grown thereon. Accordingly, the interaction between various inorganic materials and cells may be studied based upon chemical adhesion rather than mechanical interlocking. The predetermined surface roughness is preferably less about 10 μm root-mean-square, and more preferably less than about 1 μm root-mean-square. The relatively smooth growth surface is preferably obtained by thermal vacuum evaporation and deposition, followed by annealing of the as-deposited film.

17 Claims, 1 Drawing Sheet

UNITED STATES PATENT AND TRADEMARK OFFICE
CERTIFICATE OF CORRECTION

PATENT NO. : 5,538,887

DATED : July 23, 1996

INVENTOR(S) : Peindl et al.

Page 3 of 5

It is certified that error appears in the above-identified patent and that said Letters Patent is hereby corrected as shown below:

Fig. 1.
(PRIOR ART)

UNITED STATES PATENT AND TRADEMARK OFFICE
CERTIFICATE OF CORRECTION

PATENT NO. : 5,538,887　　　　　　　　　　　　　Page 4 of 5
DATED : July 23, 1996
INVENTOR(S) : Peindl et al.

It is certified that error appears in the above-identified patent and that said Letters Patent is hereby corrected as shown below:

UNITED STATES PATENT AND TRADEMARK OFFICE
CERTIFICATE OF CORRECTION

PATENT NO. : 5,538,887  Page 5 of 5
DATED : July 23, 1996
INVENTOR(S) : Peindl et al.

It is certified that error appears in the above-identified patent and that said Letters Patent is hereby corrected as shown below:

Fig. 3.